(12) United States Patent
Karle et al.

(10) Patent No.: US 9,084,660 B2
(45) Date of Patent: Jul. 21, 2015

(54) INHALER

(75) Inventors: Joachim Karle, Ingelheim am Rhein (DE); Albrecht Fenner, Ingelheim am Rhein (DE); Bastian Fischer, Ingelheim am Rhein (DE); Frank Herrmann, Ingelheim am Rhein (DE); Holger Krenz, Ingelheim am Rhein (DE); Nicole Mohren, Ingelheim am Rhein (DE)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 618 days.

(21) Appl. No.: 13/322,249

(22) PCT Filed: Jun. 14, 2010

(86) PCT No.: PCT/EP2010/003522
§ 371 (c)(1),
(2), (4) Date: Jan. 19, 2012

(87) PCT Pub. No.: WO2010/149280
PCT Pub. Date: Dec. 29, 2010

(65) Prior Publication Data
US 2012/0103326 A1 May 3, 2012

(30) Foreign Application Priority Data
Jun. 25, 2009 (EP) .................................. 09008341

(51) Int. Cl.
*A61D 7/04* (2006.01)
*A61M 11/02* (2006.01)
(Continued)

(52) U.S. Cl.
CPC .................. *A61D 7/04* (2013.01); *A61M 11/02* (2013.01); *A61M 15/009* (2013.01);
(Continued)

(58) Field of Classification Search
CPC ............ A61M 11/06; A61M 15/0065; A61M 15/0091; A61M 15/009; A61M 15/0083; A61M 15/008; A61M 15/0081; A61M 15/0018; A61M 15/00; A61M 15/0045; A61M 15/0055; A61M 15/0036; A61M 15/004; A61M 15/0041; A61M 15/0051; A61M 15/0086; A61M 15/0016; A61M 15/0028; A61M 11/308; A61M 11/00; A61M 11/062; A61M 12/004; B05B 1/323; B05B 11/3094; B05B 11/007; B05B 11/0072; B05B 11/3091; B05B 11/0048; B05B 11/308; B05B 12/004; B05B 1/30; B05B 11/00; B05B 1/32; B05B 11/06; B05B 11/061; B05B 11/062; B05B 11/309; B05B 15/0028; A61D 7/00; G01F 11/02; G01F 11/026; B05C 17/0123; B05C 17/005; B05C 17/00579; B05C 17/00576; B05C 17/00516; B05C 17/00553; B05C 17/00559; A61F 2/46; A61B 17/8827
USPC ............. 128/200.11–200.24, 203.12, 203.15, 128/203.21; 604/184, 186, 223, 222; 606/93, 94; 222/137, 326, 386
See application file for complete search history.

(56) References Cited
U.S. PATENT DOCUMENTS 5,139,171 A * 8/1992 Mader ........................... 222/137
5,511,538 A * 4/1996 Haber et al. ............. 128/200.14
(Continued)

FOREIGN PATENT DOCUMENTS

EP 0 537 991 A2 4/1993
EP 1 844 805 A1 10/2007
(Continued)

*Primary Examiner* — Annette Dixon
(74) *Attorney, Agent, or Firm* — Roberts Mlotkowski Safran & Cole, P.C.; David S. Safran

(57) ABSTRACT

An inhaler for the propellant-free nebulization of a medicament preparation produces a low speed aerosol. The inhaler is combined with an add-on device for intermediate storage of the aerosol produced. The inhaler has a tensioning device for the one-handed tensioning of a drive spring and release thereof. The inhaler is provided with a dispensing device for large animals.

7 Claims, 6 Drawing Sheets

Figure 1:
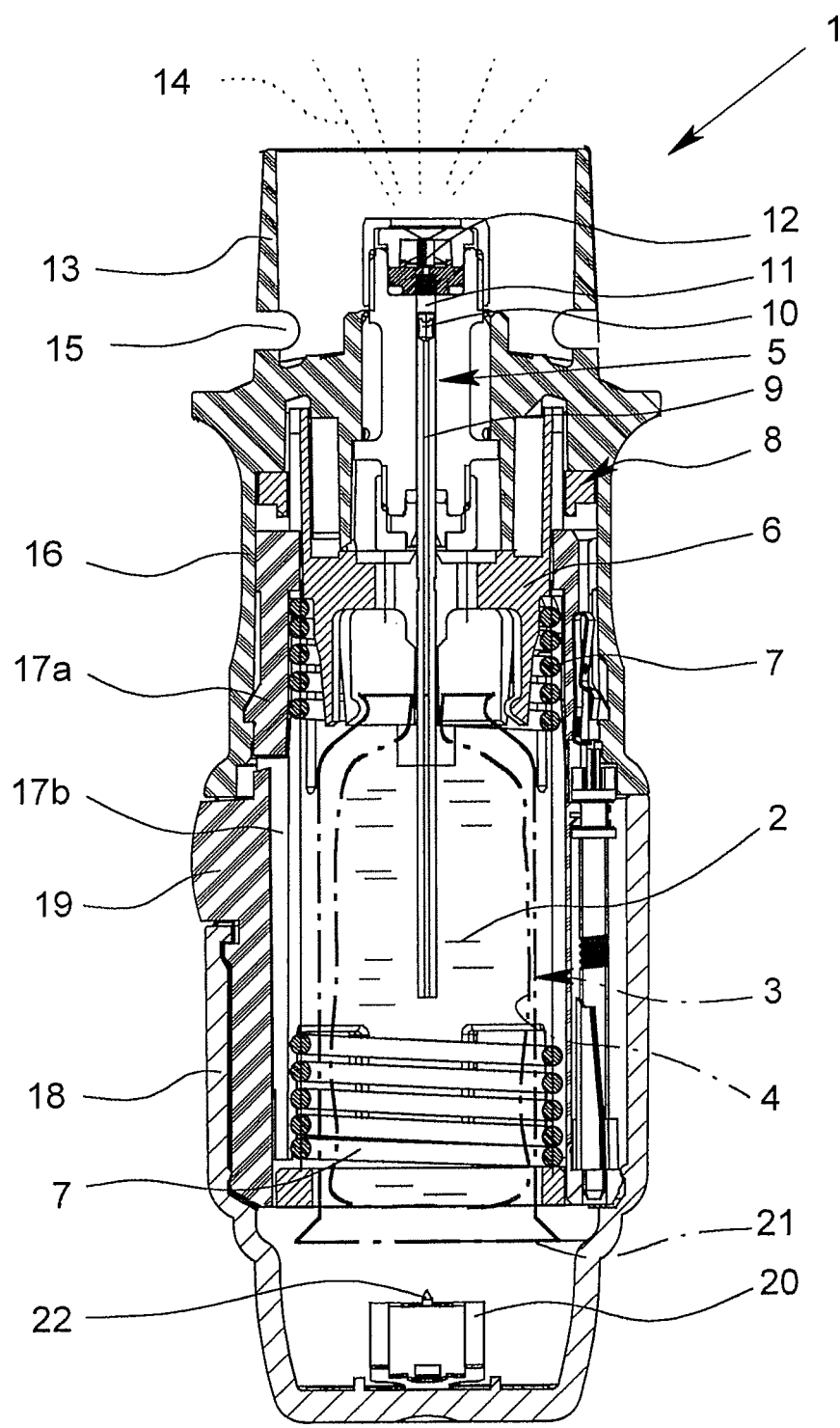

(51) Int. Cl.
  *A61M 15/08* (2006.01)
  *A61M 15/00* (2006.01)
  *A61M 16/00* (2006.01)

(52) U.S. Cl.
  CPC ...... *A61M 15/0015* (2013.01); *A61M 15/0035* (2013.01); *A61M 15/0086* (2013.01); *A61M 15/08* (2013.01); *A61M 2016/0024* (2013.01); *A61M 2205/8281* (2013.01); *A61M 2250/00* (2013.01)

(56) References Cited

U.S. PATENT DOCUMENTS

| | | | |
|---|---|---|---|
| 5,666,948 A | | 9/1997 | Matson |
| 5,740,794 A | * | 4/1998 | Smith et al. ............... 128/203.15 |
| 5,785,049 A | * | 7/1998 | Smith et al. ............... 128/203.15 |
| 5,833,988 A | | 11/1998 | Friden |
| 5,964,416 A | | 10/1999 | Jaeger et al. |
| 6,089,228 A | * | 7/2000 | Smith et al. ............... 128/203.15 |
| 6,257,233 B1 | * | 7/2001 | Burr et al. ............... 128/203.15 |
| 6,401,712 B1 | | 6/2002 | von Schuckmann |
| 6,543,448 B1 | * | 4/2003 | Smith et al. ............... 128/203.15 |
| 6,546,929 B2 | * | 4/2003 | Burr et al. ............... 128/203.15 |
| 6,901,929 B2 | * | 6/2005 | Burr et al. ............... 128/203.15 |
| 6,988,496 B1 | | 1/2006 | Eicher et al. |
| 7,077,126 B2 | | 7/2006 | Kummer et al. |
| 7,275,534 B2 | | 10/2007 | Childers et al. |
| 7,422,013 B2 | * | 9/2008 | Burr et al. ............... 128/200.23 |
| 7,779,836 B2 | | 8/2010 | Andersson et al. |
| 2005/0183718 A1 | | 8/2005 | Wuttke et al. |

FOREIGN PATENT DOCUMENTS

| | | |
|---|---|---|
| WO | 94/17753 A1 | 8/1994 |
| WO | 01/35856 A1 | 5/2001 |
| WO | 01/78818 A2 | 10/2001 |
| WO | 2004/091704 A1 | 10/2004 |
| WO | 2005/079997 A1 | 9/2005 |
| WO | 2008/067254 A2 | 6/2008 |
| WO | 2009/044172 A1 | 4/2009 |

* cited by examiner

INHALER

BACKGROUND OF THE INVENTION

1. Field of the Invention

The present invention relates to portable inhaler for propellant-free metered nebulization of a medicament preparation, having a pressure generator, and having an expulsion nozzle for delivering the nebulized medicament preparation as an aerosol. In particular, the invention relates to an inhaler that is constructed as a soft mist inhaler.

2. Description of Related Art

The present invention relates, in particular, to a so-called soft mist inhaler (SMI), i.e., an inhaler that produces a spray mist (aerosol) that spreads out only relatively slowly. Inhalers of this kind are, in particular, inhalers in which an aerosol is delivered at a speed of less than 2 m/s, preferably about 1.6 m/s or less and most preferably less than 1 m/s (in each case, measured at a distance of 10 cm from a expulsion nozzle) and/or wherein the delivery or nebulization of a dose—of preferably 10 to 50 μl of a medicament preparation—lasts longer than 0.7 s, particularly about 1 s or longer.

International Patent Application Publication WO 2005/079997 A1 and corresponding U.S. Pat. No. 7,571,722 disclose an inhaler which represents an SMI of the type to which present invention is directed. The known inhaler comprises, as the reservoir for a medicament preparation that is to be nebulized, an insertable rigid container having an inner bag containing the medicament preparation and a pressure generator with a drive spring for conveying and nebulizing the medicament preparation. Nebulization takes place without the use of propellant gas, namely by the force of the drive spring.

A problem with inhalers and SMIs in general is that the triggering of the nebulization of the medicament preparation and the intake of breath have to be coordinated. This may be difficult for the individual user. This tends to be a problem with SMIs on account of the relatively long nebulization time for each dose. Therefore, SMIs have not been used, up to now, for people with coordination problems, such as small children, or for animals, particularly large animals, such as horses.

International Patent Application Publication WO 2004/091704 A1 discloses an add-on device for the intermediate storage of a nebulized medicament preparation in a chamber. The add-on device is used in a so-called metered dose inhaler (MDI). An MDI comprises a pressurized container which contains the medicament preparation that is to be nebulized as well as a propellant gas. On actuation, the propellant gas causes the medicament preparation to be dispensed at comparatively high pressure and correspondingly high speed and with a high mass flow. Therefore, the delivery takes place over a very short time and lasts, in particular, for less than 0.4 s, usually for about 0.15-0.36 s.

The MDI's short duration of delivery is disadvantageous for inhalation as the intake of breath for inhalation normally takes considerably longer. The relatively high speed of more than 2 m/s, in many cases up to or over 8 m/s, at which the aerosol is usually delivered by an MDI, is also disadvantageous for inhaling into the lungs as the particles (droplets) of the aerosol are largely deposited on the walls of the user's throat when inhaled directly because of the high speed.

The known add-on device is intended for an MDI and serves to slow down the aerosol, particularly by increasing the flow distance. For this reason add-on devices of this kind are also known as spacers. Moreover, the add-on device serves for intermediate storage of the aerosol produced.

International Patent Application Publication WO 01/78818 A2 discloses an inhaler for the nose. The inhaler has a manually operable pump bottle and an adapter mounted thereon with a chamber for intermediate storage of an aerosol produced. The pump bottle is not an SMI in the sense of the present invention. Rather, the pump bottle has to be operated briefly and forcefully in order to achieve reasonable nebulization, so that the characteristics correspond to those of a uDI if, indeed, the pump bottle is able to produce an aerosol comprising the very small droplets that are desirable for inhalation into the lungs.

International Patent Application Publication WO 94/17753 A1 discloses an inhalation device for large animals, such as horses. The inhalation device comprises a uDI which delivers an aerosol into an add-on device having a tubular portion. The aerosol is sprayed in the longitudinal direction of the tubular portion. A soft adaptor which is designed to be introduced into a horse's nostril can be connected to the tubular portion. According to an alternative embodiment the inhalation device comprises a handle with an associated, manually operated, pivotable trigger element. When the trigger element is operated, the MDI is pushed in a linear manner, thereby opening a metering valve in the MDI and delivering aerosol into the tubular portion. A disadvantage of MDIs is that the nebulization uses propellant gas. Operation is also a problem in that the direction in which the trigger element is manually operated runs parallel to the longitudinal extent of the tubular portion or add-on device, so that the operator intuitively positions himself on the side opposite the delivery end of the add-on device; however, this is most disadvantageous for administering to a horse if the user has to hold the horse at the same time.

SUMMARY OF THE INVENTION

An object of the present invention is to provide an inhaler, most preferably an SMI, by means of which the inhalation, even of aerosols delivered at low speed, is made easier and/or wherein problems of coordinating the intake of breath and the triggering of the inhaler are avoided or at least minimized and/or wherein the inhaler is suitable particularly for use with animals, preferably large animals, such as horses, and/or is suitable for more universal use.

The above object is achieved by an inhaler in accordance the below described characteristics of the present invention.

According to a first main aspect of the present invention, an inhaler, particularly in the form of an SMI, is combined with an add-on device having a chamber for intermediate storage, i.e., temporary storage, of the aerosol produced, the chamber being arranged downstream of a expulsion nozzle of the inhaler. This makes inhalation easier and/or allows more universal use, particularly in humans or animals that are unable to operate the inhaler themselves or have problems with coordinating the triggering of the inhaler and the breathing in of the aerosol.

The preferred combination of an SMI and an add-on device with a chamber for intermediate storage of the aerosol was not obvious to the skilled man in that the known spacers and adapters are, in fact, intended for MDIs or the like which, as noted above, use a propellant gas that causes the medicament preparation to be dispensed at comparatively high pressure and correspondingly high speed with a high mass flow. However, it has been found that a surprisingly improved inhalation of the active substance can be achieved by means of the add-on device, even in an inhaler that generates the aerosol to be inhaled over a relatively long period, preferably about 1 s or longer, and/or at relatively low speed, preferably less than 2 m/s, most preferably less than 1.6 m/s (measured at a distance of 10 cm from an expulsion nozzle). Coordinating the triggering of the inhaler, i.e., the production of the aerosol, and the intake of breath is made considerably easier. The aerosol is produced by the inhaler and sprayed into the chamber of the add-on device from which it can be breathed in.

The proposed solution permits better defined inhalation of the active substance with a fraction of active substance deposited in the lungs that is higher on average and/or fluctuates less than in an MDI. This permits improved treatment or the use of different medicament preparations which have to be metered more accurately. Finally, the SMI is, as a result, more versatile.

Preferably, the aerosol is introduced into the chamber at right angles to a main dispensing direction and/or the longitudinal direction of the chamber. This results in a compact construction and/or enables a conventional inhaler to be used which delivers the aerosol in the longitudinal direction.

Particularly preferably, the add-on device comprises an inlet valve for admitting supply air into the chamber and for blocking flow in the opposite direction. This prevents the unwanted blowing of the aerosol out of the chamber during an outward breath. Particularly preferably, the inlet valve is arranged upstream of a connector for admitting the aerosol into the chamber. This avoids the aerosol having to flow through the inlet valve and being impeded by it.

Preferably, the add-on device has a breath intake indicator for indicating the airflow through the chamber in the dispensing direction. This assists with the use of the inhaler or the triggering of the nebulization, as it thus indicates the intake of breath to the operator or user. This assists with coordination, and therefore, promotes the universal use of the inhaler, for example, in people who cannot initiate the nebulization themselves, or in animals.

According to a preferred embodiment, the add-on device comprises a dispensing connector for connecting to a dispensing device only in a defined rotational position. Alternatively or additionally, the inhaler comprises a trigger element which is arranged on the long side with respect to a main dispensing direction and/or longitudinal extent of the chamber. Thus, a defined arrangement can be achieved which allows particularly simple operation.

In particular, this arrangement is convenient when used for horses as the inhaler with the add-on device can be held projecting laterally at right angles next to the horse's head, while the inhaler engages in the corresponding nostril of the horse by means of a main dispensing device and the operator can stand next to the horse, looking in the direction parallel to the horse, so that the trigger element faces the operator. This allows very simple intuitive operation, in which the operator can position himself next to the horse, in particular on its left, in the manner which is tried and tested for horses, and can see the inhaler. At the same time, the operator can hold the horse with one hand on the horse's head or neck and in particular on a halter or the like.

Preferably, the dispensing device has a larger diameter or cross-section than the chamber. Thus additional intermediate storage can be obtained.

According to a second, independently achievable main aspect of the present invention, the inhaler comprises means for mechanically cleaning an expulsion nozzle. The means comprises in particular a swivel element and/or a cleaning element. This enables the inhaler to be used more universally, for example, for animals, particularly large animals such as horses, while any contamination of the expulsion nozzle which might have a negative effect on the dosing or nebulization can be avoided or eliminated by the proposed cleaning means.

According to a third, also independently achievable main aspect of the present invention, the inhaler is constructed to be operated with one hand, in particular to allow one-handed tensioning of a spring or other energy store which brings about the actual nebulization. Moreover, the nebulization can then, preferably, also be triggered one-handedly by an operator, in particular. This permits particularly simple handling of the preferably propellant-free inhaler so that it can be used more universally, particularly also for people with coordination problems and/or for animals, preferably large animals, especially horses.

The aspects and features mentioned above may be implemented independently of one another, in particular independently of the other features of the invention, and also in any desired combination.

Further advantages, features, properties and aspects of the present invention will be apparent from the following description with reference to the accompanying drawings.

BRIEF DESCRIPTION OF THE DRAWINGS

FIG. 1 shows a schematic section through an inhaler in the untensioned state;

FIG. 2 shows a schematic section through the inhaler in the tensioned state, rotated through 90° compared with FIG. 1;

FIG. 3 shows a schematic view of the inhaler with the add-on device connected;

FIG. 4 shows a schematic section through the inhaler with the add-on device and a dispensing device in the state of attachment to a horse's nostril;

FIG. 5 shows a side view of a modified embodiment of the inhaler with the add-on device connected; and FIG. 6 shows a plan view of the inhaler according to FIG. 5.

DETAILED DESCRIPTION OF THE INVENTION

In the figures, the same reference numerals have been used for identical or similar parts, while corresponding or comparable properties and advantages are obtained even if the respective description has not been repeated.

FIGS. 1 and 2 show a portable inhaler for propellant-free nebulization of a medicament preparation 2 in schematic view in the untensioned state (FIG. 1) and in the tensioned state (FIG. 2). FIGS. 1 and 2 show the inhaler 1 with a container 3 containing the medicament preparation 2.

On nebulization of the, preferably a liquid, medicament preparation 2, an aerosol 14 destined for the lungs is formed (FIG. 1) which can be breathed in or inhaled by a user or patient (not shown), such as a human being or an animal, preferably a large animal, particularly a horse. Usually, the inhalation takes place at least once a day, more particularly several times a day, preferably at predetermined intervals, depending, in particular, on the complaint.

In particular, the inhaler 1 is constructed as a soft mist inhaler as described initially above.

The inhaler 1 comprises the preferably insertable and optionally replaceable container 3 with the medicament preparation 2. The container 3 thus forms a reservoir for the medicament preparation 2 that is to be nebulized. Preferably, the container 3 contains a sufficient amount of medicament preparation 2 or active substance for several doses of the medicament preparation 2, i.e., to allow a number of nebulizations or applications. A typical container 3, as disclosed in International Patent Application Publication WO 96/06011 A1 and corresponding U.S. Pat. No. 5,833,088, holds a volume of about 2 to 10 ml. With respect to the preferred structure of the container 3, reference may be made to International Patent Application Publication WO 00/49988 A2 and corresponding U.S. Pat. No. 6,988,496 for additional information.

The container 3 is preferably substantially cylindrical or cartridge-shaped and after the inhaler 1 has been opened, the container can be inserted therein from below and optionally replaced. It is preferably of rigid construction, the medicament preparation 2 being contained, in particular, in a collapsible bag 4 in the container 3.

The inhaler 1 also comprises a conveying device or a pressure generator 5, for conveying and nebulizing the medicament preparation 2, particularly in a predetermined and optionally adjustable dosage amount in each case, i.e., for metered nebulization or nebulization in a plurality of defined doses. One dose may be administered on each actuation of the inhaler 1.

The inhaler 1 or pressure generator 5 is particularly designed so that the conveying, pressure generation and/or nebulization take place without the use of propellants, mechanically and/or by the energy or force of an energy store, particularly a spring store, most preferably by the spring force of a drive spring 7, in the embodiment shown. However, other design solutions are also possible.

The inhaler 1 or pressure generator 5 comprises, in particular, a holder 6 for the container 3, the associated drive spring 7, which is only partly shown, preferably having an associated trigger element 8 which is manually operable to release it, a conveying element, preferably a conveying tube 9 in the form of a capillary, with an optional valve, particularly a non-return valve 10, a pressure chamber 11 and/or an expulsion nozzle 12, particularly in the region of an outlet or mouthpiece 13.

The container 3 is fixed in the inhaler 1 by means of the holder 6, particularly by a clamping or latching action, such that the conveying tube 9 protrudes into the container 3. The holder 6 may be constructed such that the container 3 can be exchanged.

For tensioning the drive spring 7, the inhaler 1 or pressure generator 5 preferably comprises a tensioning device. When the drive spring 7 is axially tensioned, the holder 6 with the container 3 and the conveying tube 9 is moved downwards with reference to the orientation shown in the figures and the medicament preparation 2—or more precisely the next dose—is sucked out of the container 3 into the pressure chamber 11 of the pressure generator 5 through the non-return valve 10.

During the subsequent relaxation of the drive spring 7 after operation of the trigger element 8, the medicament preparation 2 in the pressure chamber 11 is placed under pressure by releasing the tension on the drive spring 7 thereby moving the conveying tube 9 back up, with the non-return valve 10 now closed, so that the conveying tube 9 now acts as a pressure ram (piston). This pressure expels the medicament preparation 2 through the expulsion nozzle 12, where it is nebulized into the preferably inhalable aerosol 14, as shown in FIG. 1.

The user or patient (not shown) can inhale the aerosol 14, while preferably supply air can be sucked into the connector 13 through at least one supply air opening 15.

During the nebulization process, the container 3 is moved back into its original position by the drive spring 7. The container 3 thus performs a lifting movement during the tensioning process and during the nebulization process.

The inhaler 1 comprises, in particular, a first housing part (upper part) 16 and an inner part 17 which is rotatable relative thereto (FIG. 2), the inner part 17 having an upper part 17a and a lower part 17b (FIG. 1). The inhaler 1 also comprises a second housing part (lower part) 18, which, in particular, is manually operable or rotatable, and is releasably attached to, in particular pushed onto, the inner part 17, preferably by means of a safety closure or retaining element 19.

In particular, the safety closure or retaining element 19 is constructed such that accidental opening of the inhaler 1 or removal of the second housing part 18 is prevented. In particular, in order to release the second housing part 18, the retaining element 19 has to be pressed in against spring force. In order to insert and/or replace the container 3, the second housing part 18 can be detached from the inhaler 1. The second housing part 18 preferably forms a cap-like lower housing part and/or engages around or over a lower free end portion of the container 3.

Figure 2:
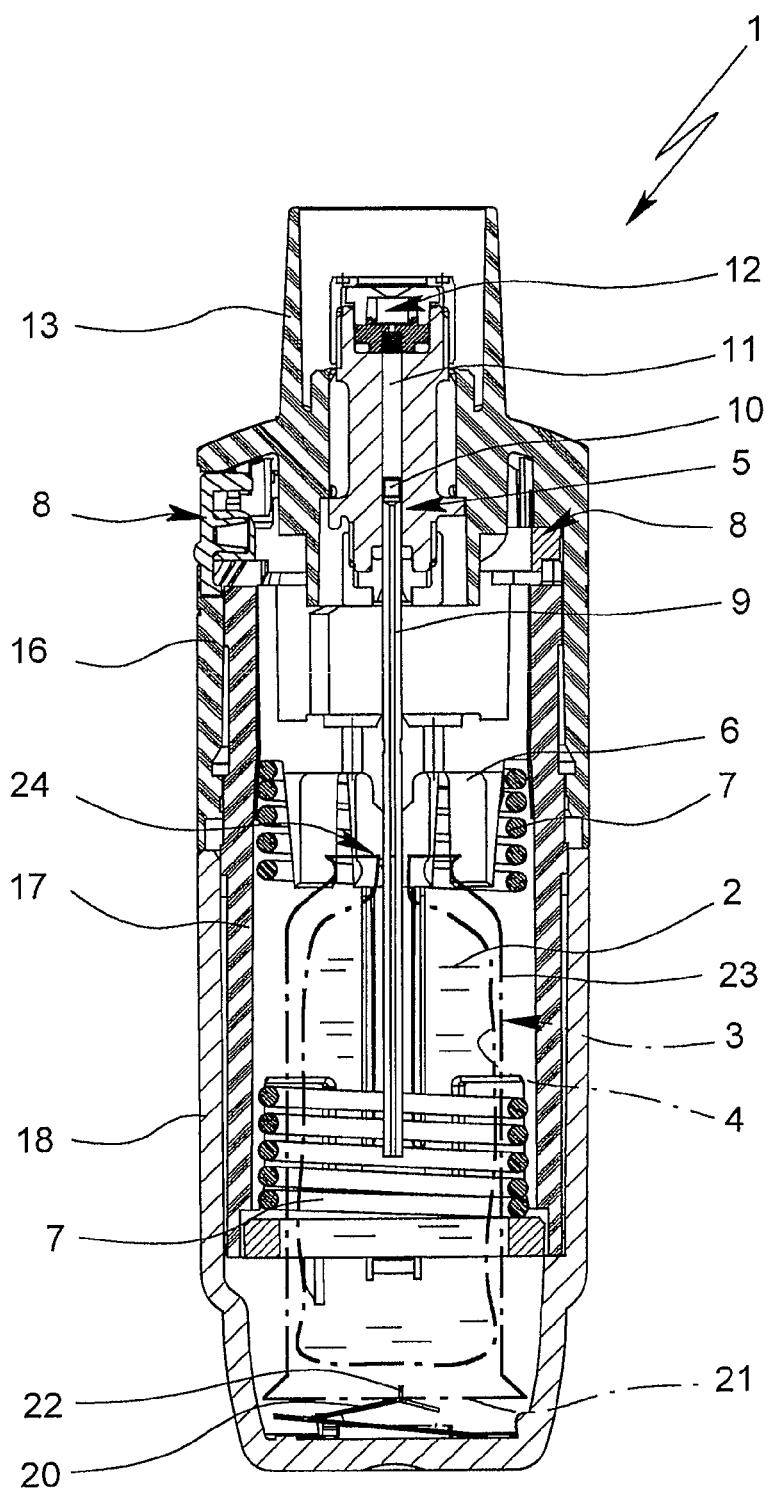

The second housing part 18 can be rotated relative to the first housing part 16, whereby the inner part 17 is also rotated. In this way, the drive spring 7 is tensioned in the axial direction by means of a gear (not shown in detail) acting on the holder 6, which acts indirectly or directly, in particular, via a screw thread on the holder 6. During tensioning, the container 3 is moved axially downwards or with its end portion (further) into the second housing part 18 or towards the end face thereof, until the container 3 assumes an end position as shown in FIG. 2. In this state, the drive spring 7 or inhaler 1 is clamped and locked.

In the embodiment shown, the tensioning device for tensioning the drive spring 7 or other energy or spring store comprises, in particular, at least one rotatable part, such as the second housing part 18 and/or inner part 17, and in this case, preferably, also a gear for converting the rotary movement into linear movement, in this case, axial, tensioning movement. Preferably, the rotary movement is always continued in the same direction of rotation during tensioning; therefore, reverse rotation is not required. However, other design solutions are also possible.

The inhaler 1 preferably has a device for forcibly ventilating the container 3.

When tensioning first takes place, the base of container 3 is preferably pierced or opened. In particular, an axially acting spring 20 arranged in the housing part 18 comes to abut on the container base 21 and with a piercing element 22 pierces the container 3, a gastight seal is created in the base for ventilation purposes when contact is first made.

The device for forcible ventilation is thus formed, in this case, by the piercing element 22, which is held or formed by the spring 20. However, other design solutions are also possible.

It should be noted that, during the piercing, for ventilation purposes, only the outer shell of the container 3 is opened. The bag 4 containing the medicament preparation 2 remains undamaged. As the medicament formulation 2 is removed from the bag 4 through the conveying tube 9, the flexible bag 4 collapses. For pressure equalization, ambient air can flow into the container 3 through the ventilation or piercing opening.

In order to use the inhaler 1, first of all the container 3 has to be inserted. This is preferably done by removing or pulling out the second housing part 18. The container 3 is then axially inserted or pushed into the inner part 17. At the same time, the container 3 is opened at the head end or attached. This is done by means of the conveying element, i.e., the conveying tube 9, which pierces a seal preferably provided at the head end of the container 3, is then inserted into the interior of the bag 4 through a septum at the top end of the container 3. Thus, a fluidic connection between the container 3, or more accurately between the bag 4 in the container 3, is produced via the conveying tube 9 to the pressure generator 5 or pressure chamber 11.

Then, the second housing part 18 is pushed on again. The inhaler 1 can now be tensioned for the first time. At this stage, the container 3 is then pierced at its base by the piercing element 22, i.e., forcibly ventilated, as explained previously.

After the container 3 has been inserted and fluidically connected and before it is used for the first time, the inhaler 1 is preferably tensioned and triggered several times. This so-called priming displaces any air present in the medicament preparation 2, in the conveying tube 9 and in the pressure generator 5 to the expulsion nozzle 12. The inhaler 1 is then ready for inhalation.

The quantity of medicament preparation 2 delivered per spray or nebulization process is preferably about 10 µl to 50 more particularly about 10 µl to 20 µl, most preferably about 15 µl.

The drive spring 7 is preferably installed in a biased state in order to achieve a high spring pressure. In fact, in the proposed inhaler 1, the pressurization and conveying of the medicament preparation 2 during the nebulization process takes place preferably only by spring force, and more particularly, only by the force of the drive spring 7.

The inhaler 1 is preferably constructed such that the medicament preparation 2 in the pressure generator 5 or in the pressure chamber 11 reaches a pressure of 5 MPa to 60 MPa, particularly about 10 MPa to 50 MPa during delivery. Particularly preferably, during the delivery or nebulization of the medicament preparation 2, a pressure of about 5 MPa to 60 MPa, more particularly about 10 to 30 MPa, is reached at the expulsion nozzle 12 or at the nozzle openings thereof. The medicament preparation 2 is then converted into the aerosol 14, the droplets of which have an aerodynamic diameter of up to 20 µm, preferably about 3 µm to 10 µm. The nebulizing activity or nebulizing effect is achieved or further assisted by preferably intercepting jets delivered by the expulsion nozzle 12.

The inhaler 1 is preferably constructed such that the aerosol 14 is delivered at low speed, particularly at a speed of less than 2 m/s, most preferably about 1.6 m/s or less (in each case measured at a distance of 10 cm from the expulsion nozzle 12). The inhaler 1 is thus preferably in the form of an SMI. The low dispensing speed can be obtained or assisted by intercepting jets of the medicament preparation 2, which are delivered by the expulsion nozzle 12 and/or by a suitable choice of spring force.

Particularly preferably, the construction of the inhaler 1 is such that the aerosol generation lasts for more than 0.7 s, preferably substantially 1 s or longer, in particular for more than 1.5 s. The time taken to nebulize a dose or to actuate the inhaler 1 is thus preferably more than 0.75, more particularly about 1 s or more.

The inhaler 1 preferably has an add-on device 23 with a chamber 24 for receiving and/or intermediately storing the aerosol 14 produced by the inhaler 1, as is shown in a schematic section according to FIG. 4.

The chamber 24 is arranged or adapted to be arranged downstream of the expulsion nozzle 12. It serves to receive and/or intermediately store the aerosol 14 produced by the inhaler 1.

Preferably, the add-on device 23 or its chamber 24 is at least substantially tubular, cylindrical, elongate or conical in construction.

The add-on device 23 preferably comprises a connector 25 for mechanical and/or fluidic connection to the inhaler 1 or its connecting member 13. The add-on device 23 is releasably or non-releasably connectable to the inhaler 1 or connecting member 13, for example, by pushing on, clamping on or latching. In the embodiment shown, the aerosol 14 is introduced into the chamber 24 at right angles or perpendicularly to a longitudinal dimension or main dispensing direction in the chamber 24. FIG. 4 schematically shows how the aerosol 14 is delivered from the inhaler 1 through the lateral connector 25 into the chamber 24.

The inhaler 1 or add-on device 23 preferably comprises a dispensing device 27, such as an adapter, that can be attached at the outlet end.

The add-on device 23 preferably comprises, at the outlet end, a dispensing connector 26 particularly for connecting to the associated dispensing device 27, as schematically shown in FIG. 4.

The add-on device 23 or chamber 24 preferably has an inlet opening 28 for admitting supply air (ambient air). The inlet opening 28 is preferably provided on the end of the add-on device 23 or chamber 24 opposite the dispensing connector 26, and/or upstream of the connector 25. However, other arrangements are also possible.

The connector 25 for connecting to the inhaler 1 or for admitting the aerosol 14 produced by the inhaler is preferably arranged between the two ends of the add-on device 23 or chamber 24 or between the dispensing connector 26 and the inlet opening 28. In particular, the inhaler 1 is arranged on the side of the add-on device 23 or chamber 24 or extends at right-angles or perpendicularly to the longitudinal direction or main dispensing direction thereof. However, other geometric arrangements are also possible.

Preferably, the chamber 24 has a larger cross section than the connecting member 13 and/or widens out at least in parts towards a delivery end or connector or free end of the add-on device 23. This ensures that the aerosol 14 strikes a wall of the chamber 24 over the smallest possible area. In this way, it is possible to minimize the deposition or settling of the nebulized medicament preparation 2 on the wall of the chamber.

Preferably, the add-on device 23 or chamber 24 comprises an inlet valve 29 for admitting supply air into the chamber 24, the inlet valve 29 preferably blocking or throttling the flow in the opposite direction, in particular so that during an outward breath, air cannot escape from the chamber 24 through the inlet opening 28 and pass into the atmosphere. In the embodiment shown, the inlet valve 29 is preferably in the form of a non-return (one-way check) valve or flap-type valve, which may or may not be biased into the closed position. However, other design solutions are also possible.

Preferably, at least when the add-on device 23 is attached, the optional supply air openings 15 in the inhaler 1 are closed or provided with an associated supply air valve so that no air can be released from the chamber 24 through the connector 25 and the supply air opening(s) 15.

The inhaler 1 or the add-on device 23 preferably comprises a breath intake indicator 30 for indicating a flow of air particularly in the chamber 24 in the dispensing direction. The breath intake indicator 30 thus indicates when the patient breathes in or inhales, in particular when air flows from the inlet opening 28 through the chamber 24 to the dispensing connector 26. In the embodiment shown, the breath intake indicator 30 preferably comprises a pivotably mounted part that is leaf-shaped, and/or can be deflected or pivoted by the flow of air. However, other design solutions are also possible.

Preferably, the add-on device 23 or its housing or the walls of the chamber 24 are transparent at least in parts or completely transparent, in order that the breath intake indicator 30 can be seen from outside and/or so that any contamination or the like can be detected from outside.

Preferably, the chamber 24 is larger in diameter or cross-section than the connecting member 13, particularly by a factor of 1.5 or more, most preferably by a factor of 2 or more. This reduces the tendency of the aerosol 14 to be deposited on the walls of the chamber 24.

The chamber 24 preferably has a volume of more than 0.1 l, particularly more than 0.2 l, most preferably about 0.2 to 0.6 l. In particular, the add-on device 23 or the size of the chamber 24 is adapted to the inhaler 1 such that the aerosol 14 produced on actuation of the inhaler 1 can be at least substantially entirely received by the chamber 24 without the aerosol 14 or the nebulized medicament preparation 2 essentially being deposited or settling on the inner wall of the chamber.

The add-on device 23 is preferably at least substantially rigid in construction. However, the add-on device 23, the chamber 24 or its housing may theoretically also be flexible, inflatable and/or telescopic in construction, in order to minimize the space taken up when not in use and/or for transportation purposes, in particular.

The add-on device 23 is preferably not rotatable relative to the inhaler 1. In the embodiment shown this is achieved by the fact that the connecting member 13 of the inhaler 1 has an outer contour that is not round, but preferably is oval and to which the connector 25 is adapted accordingly. However, other design solutions are also possible.

Figure 3:
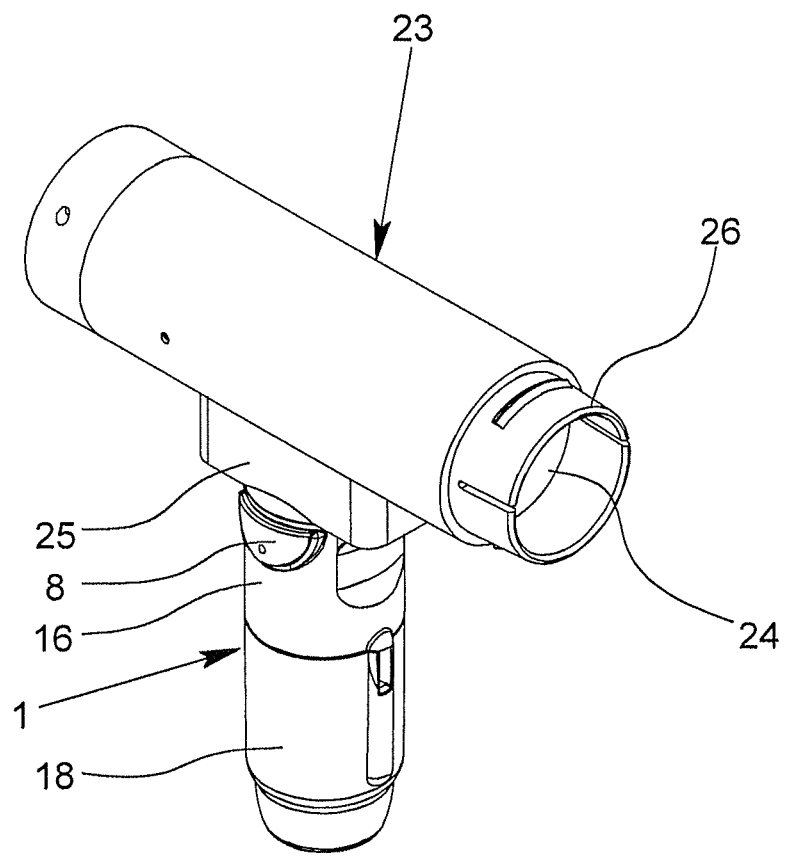

The dispensing connector 26 is preferably constructed so that the dispensing device 27 can only be connected to the add-on device 23 in a defined rotational position. In particular, the dispensing connector 26 comprises for this purpose at least one axial slot or the like, as schematically shown in FIG. 3, into which the dispensing device 27 can engage by means of a rib, a projection or a strut, for example. However, other design solutions are also possible.

Preferably, the dispensing device 27 can be connected to the add-on device 23 by latching and/or clamping and/or by a bayonet connection or the like. However, other design solutions are also possible.

Alternatively, the dispensing device 27 may also be irremovably connected or connectable to the add-on device 23 or formed in one piece therewith or formed thereby.

Figure 4:
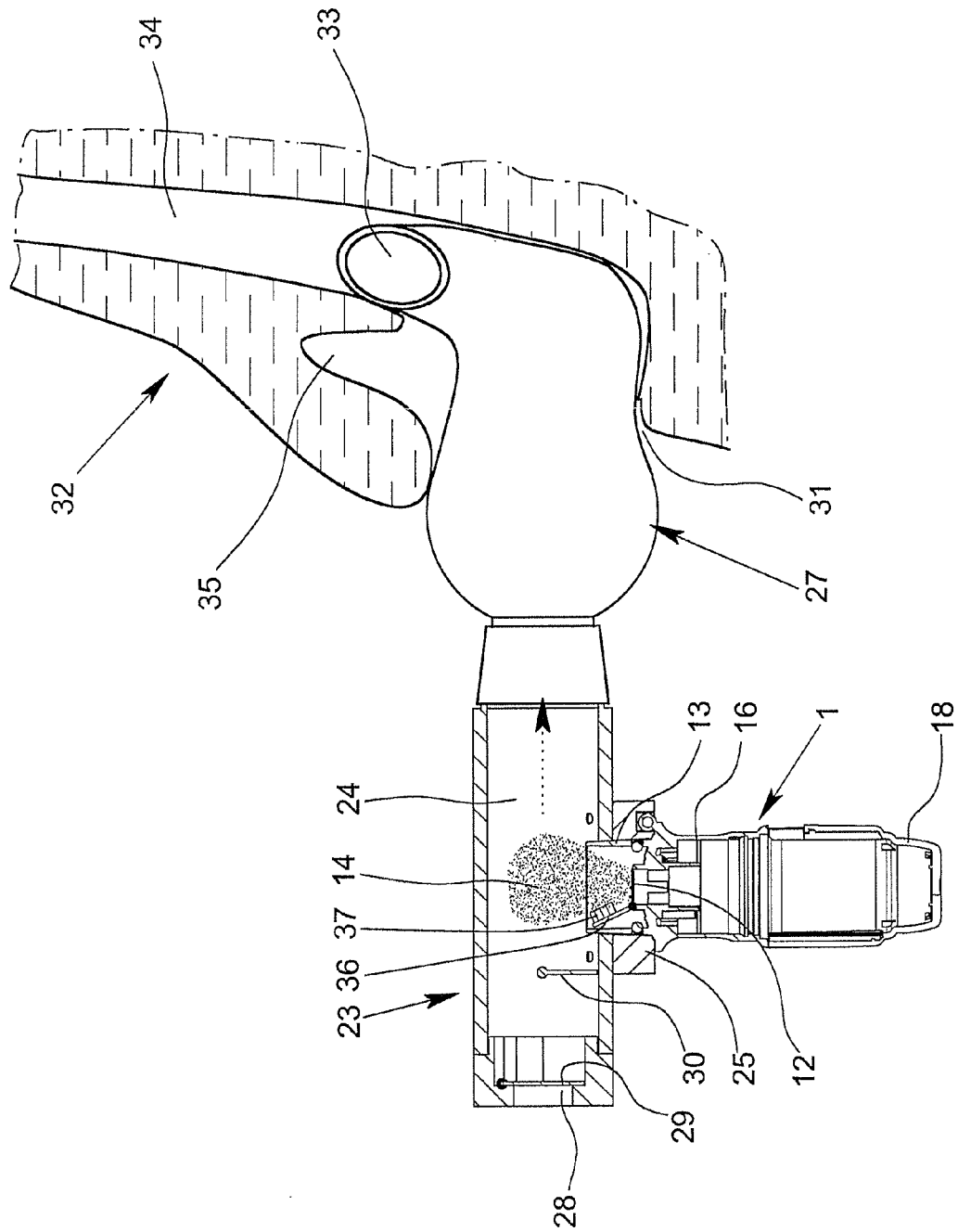

The dispensing device 27 preferably has a larger diameter or cross-section than the chamber 24, as indicated in FIG. 4.

The dispensing device 27 preferably has a soft end piece or forms such an end piece.

The dispensing device 27 is preferably constructed as a nasal adapter for insertion in a nostril 31 of a horse 32 or other animal, particularly a large animal, as schematically shown in FIG. 4. In particular, the inhaler 1 or the add-on device 23 or the dispensing device 27 is thus designed so that the aerosol 14 is prepared for inhalation by the horse 32 or other animal or large animal.

In the embodiment shown, the dispensing device 27 is designed to be inserted in the left nostril 31 of the horse 32.

The dispensing device 27 preferably comprises an outlet 33 that engages or can be inserted in the nostril 31 or a nasal passage 34 of the horse 32. Particularly preferably, the connecting device 27 is designed so that the outlet 33 always goes in the correct nasal passage 34 and does not end in a blind passage 35.

Particularly preferably, the connecting device 27 is constructed as described in WO 94/17753 A1.

The inhaler 1 is preferably connected or connectable to the add-on device 23 such that the trigger element 8 is arranged laterally, and in the representation shown in FIG. 4 on the side facing the observer and/or on the side towards which the outlet 33 opens. Preferably, the trigger element 8 is arranged so that the inlet opening 28 is to the left of it and/or the dispensing connector 26 is to the right of it.

The preferred arrangement described above makes it possible or easier for an operator (not shown) to stand to the left next to the neck or head of the horse 32 (part of the head with the nostril 31 is shown schematically in section in FIG. 4), while the operator may position himself to look straight ahead in the direction of travel of the horse 32, can hold the horse 32 with his right hand on its neck or head, particularly using a halter or the like (not shown), and with his left hand can hold the inhaler 1 in the position shown in FIG. 4 with the dispensing device 27 inserted in the nostril 31, using the thumb of his left hand, in particular, to operate the trigger element 8 for actuating the inhaler 1, i.e., for initiating a nebulization.

The operation of the inhaler 1 is made even easier if it is constructed so that it can be tensioned and triggered with one hand. In particular, it is then possible for a single operator to hold both the inhaler 1 and the horse 32 or other animal at the same time and perform a number of actuations (i.e., tensioning and triggering for one actuation in each case) with one hand. Accordingly, the operator does not have to let go of the horse 32. In addition, the inhaler 1 or its dispensing device 27 can be held continuously in fluidic connection with the horse 32 or animal during the nebulization of a number of doses.

An embodiment which allows single-handed tensioning and triggering of the inhaler 1 will be explained in more detail hereinafter by reference to the other figures.

The inhaler 1 preferably comprises means 36 for covering and/or cleaning the expulsion nozzle 12, as schematically shown in FIG. 4. Thus, any soiling of the expulsion nozzle 12 which might interfere with good nebulization and/or dosing can be prevented and/or eliminated. Such soiling may easily occur, in particular, in a rougher environment, such as in a stable or the like.

The means can preferably be operated from outside.

In the embodiment shown, the means are constructed as a swivel or pivotable element 36. However, it may also in the form of a slide, carriage or the like.

The means preferably comprise a cleaning element 37, for example, in the form of a sponge, a brush or the like. However, other design solutions are also possible here.

The means can be used, for example, to cover the expulsion nozzle 12 before any cleaning of the add-on device 23 or chamber 24. Alternatively or additionally the expulsion nozzle 12 can be cleaned, for example, after the cleaning of the add-on device 23 or chamber 24 and/or after removal of the add-on device 23 using the means or cleaning element 37.

Preferably, the inhaler 1 is connected or connectable to the add-on device 23 such that the inhaler 1 or its housing (formed in this case from the two housing parts 16 and 18) is not movable or slidable relative to the add-on device 23 or dispensing device 27 during actuation or use. This allows a simple, robust structure.

Preferably, the inhaler 1 or its housing (particularly its housing parts 16 and/or 18) comprises a grip or handle for holding the add-on device 23 and/or dispensing device 27 during use. This results in a simple and/or compact structure.

An alternative embodiment of the proposed inhaler 1 with add-on device 23 will now be described in more detail with reference to FIGS. 5 and 6. FIG. 5 shows a side view and FIG. 6 a plan view. In particular, only essential differences from the embodiment described above will be explained, which means that the previous explanations and remarks still apply correspondingly or in similar manner, even if the associated description has not been repeated.

In the alternative embodiment shown, the inhaler 1 is designed to be tensioned and released using one hand. For this purpose, a tensioning device 38 is associated with the inhaler 1. The construction in which the inhaler 1 can be tensioned and released using one hand can also be achieved independently of other aspects, in particular also independently of the add-on device 23 and/or dispensing device 27.

In the embodiment shown, the tensioning device 38 preferably also comprises a rotatable part, particularly the inner part 17 of the inhaler 1, for tensioning the drive spring 7 or other spring store or energy store.

Figure 5:
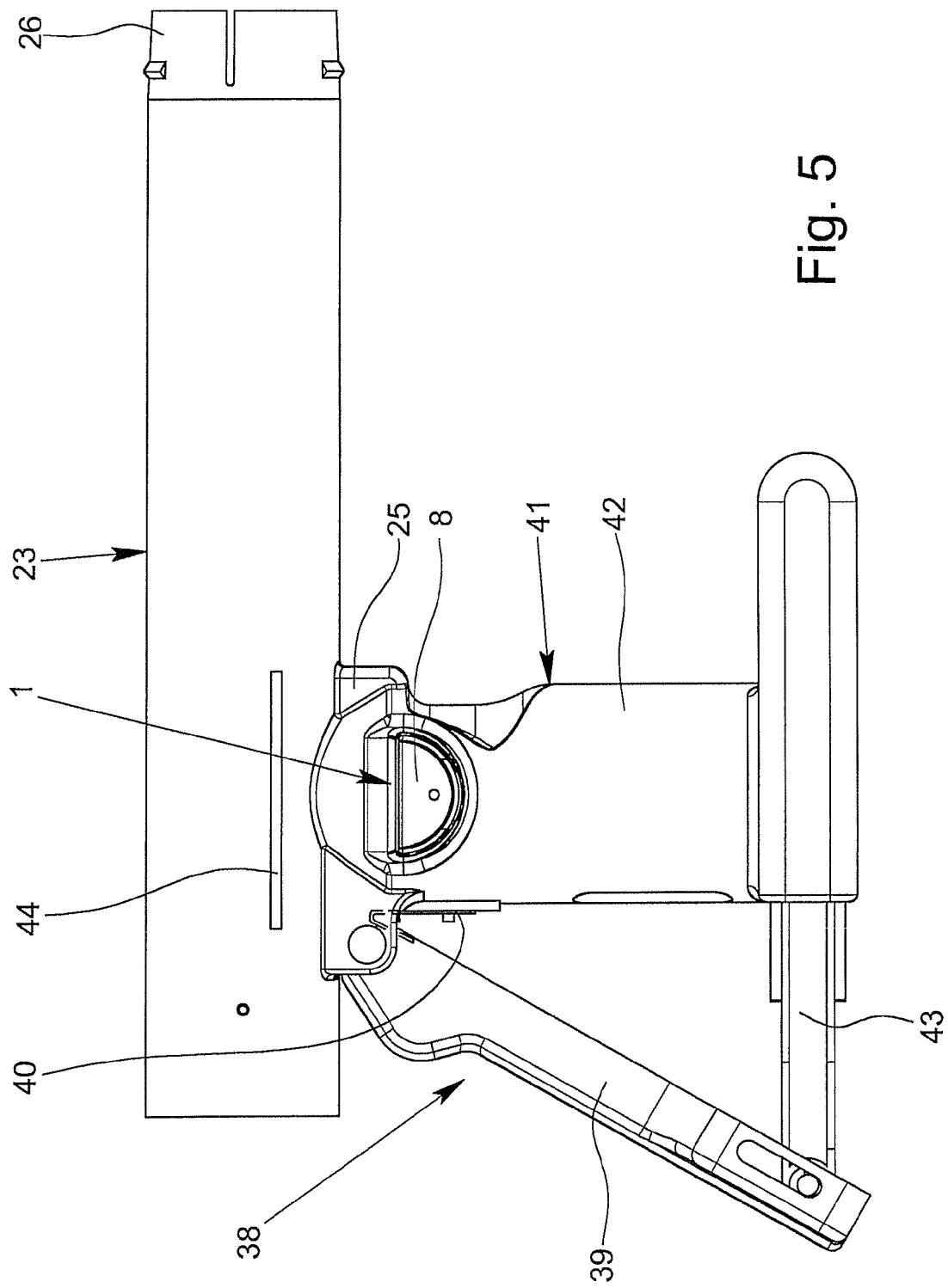
Figure 6:
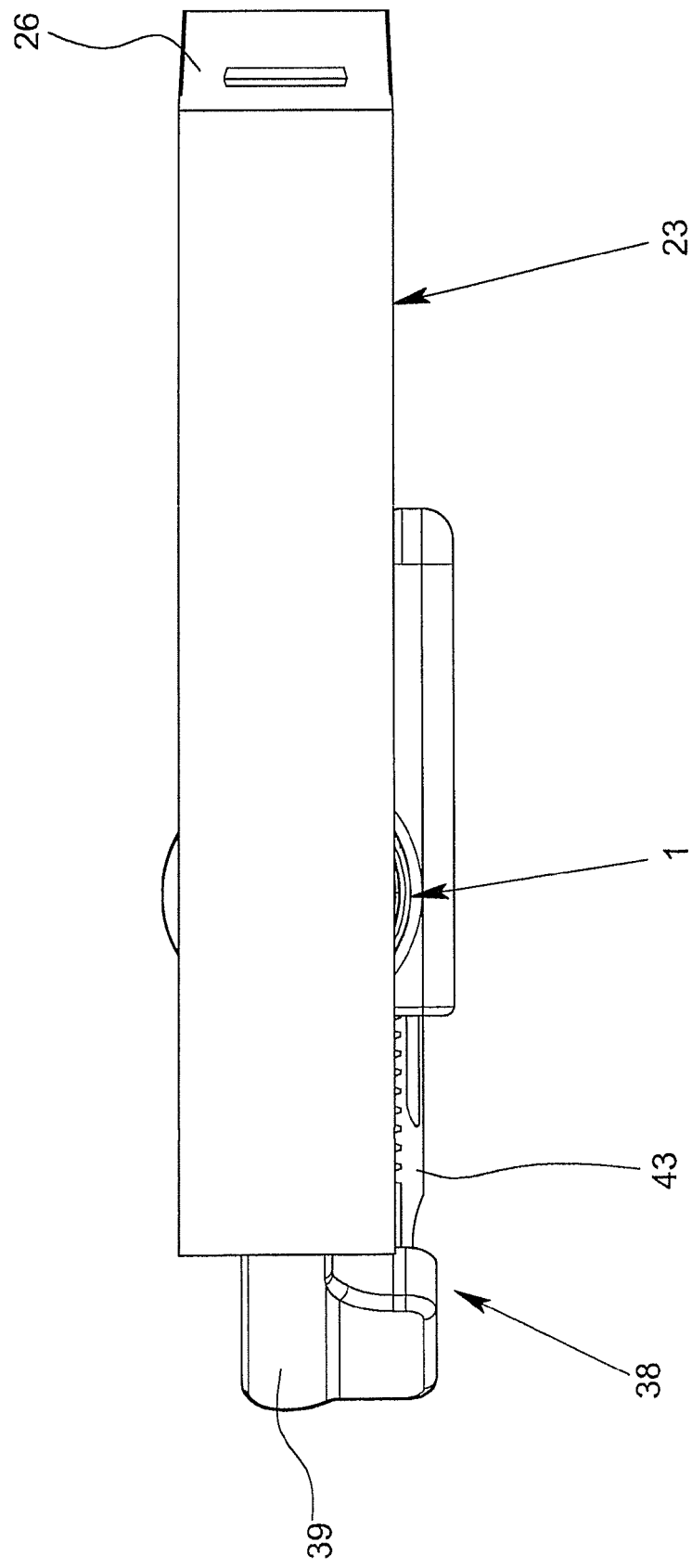

The tensioning device 38 preferably comprises a manually operable actuating element 39 which preferably pivots during actuation, in particular, counter to the force of an associated restoring spring 40. Particularly preferably, the actuating element 39 is pivotably held on the inhaler 1 or its housing and/or by the add-on device 23. Alternatively, the tensioning device 38 comprises, in particular, a housing-like receptacle 41 in the form of a housing the fits over the inhaler 1, as shown in FIG. 5. The inhaler 1 can be inserted in the receptacle 41, in particular so that the trigger element 8 can still be actuated from outside—for example, through an opening in the receptacle 41—and/or so as to enable tensioning of the drive spring 7, particularly by operation of the actuating element 39.

In the embodiment shown, the tensioning device 38 comprises a holding portion or grip member 42, which is formed in this case particularly by the outside of the receptacle 41. In the embodiment shown the inhaler 1 is thus preferably arranged in the grip member 42 or can be accommodated therein. However, other design solutions are also possible. For example, the grip member 42 may also be constructed separately or as a separate part.

The tensioning device 38 preferably comprises a coupling element 43, for converting the movement of the actuating element 39 on actuation into a driving movement—in this case for rotating the housing part 18 and/or part 17 or a gear or the like for tensioning the drive spring. In particular, the pivoting movement of the actuating element 39 is converted into a linear movement.

In the embodiment shown, the coupling element 43 is preferably constructed as a toothed rack which preferably engages, by means of corresponding teeth, in external teeth provided on the housing part 18 or inner part 17. However, other design solutions are also possible here. For example, instead of the rigid coupling element 43, a flexible coupling element may also be provided, which is guided, for example, around the housing of the inhaler 1 or the housing part 18 or inner part 17, so as to allow a particularly compact construction.

The tensioning device 38 preferably forms a construction unit which accommodates and/or holds the inhaler 1 and which preferably also holds the add-on device 23 and/or connecting device 27. However, other design solutions are also possible.

In order to tension the inhaler 1, the actuating element 39 is manually operated, preferably pivoted, in this case towards the grip member 42.

The coupling element 43 converts this pivoting movement into a linear movement in the embodiment shown. For this purpose, the coupling element 43 is guided on the receptacle 41 or on the grip member 42 to be movable only in a linear manner—for example, in the manner of a slide—and is coupled to the free end of the actuating element 39 via an oblong hole. However, other design solutions are also possible here.

The linear movement of the coupling element 43 during the tensioning of the inhaler 1 preferably runs from left to right in the view shown in FIG. 5. The linear movement causes the part 17 and/or 18 to rotate and the drive spring 7 to be tensioned.

After tensioning is complete, the drive spring 7 is secured against premature relaxation and the actuating element 39 can be released again. A preferably automatic resetting then takes place, particularly by means of the optional restoring spring 40. However, other design solutions are also possible.

After tensioning, the nebulization may be activated. In the embodiment shown, this is done by pressing the trigger element 8, which releases the holder 6 or drive spring 7, so that the force of the drive spring 7 causes the dose of medicament preparation 2 contained in the pressure chamber 11 to be nebulized through the expulsion nozzle 12—and in particular, into the add-on device 23 attached thereto. The operation is triggered, in particular, when the breath intake indicator 30 shows an intake of breath, i.e., a flow of air in the direction of the dotted arrow shown in FIG. 4. It should be noted that, in FIG. 4, the breath indicator 30 is shown in the resting position. The flow of air would cause the preferably leaf-like element to be deflected to the right, for example.

The longitudinal extent or main delivery direction of the add-on device 23 or chamber 24 preferably runs in the direction of the dotted arrow. The longitudinal extent of the inhaler 1 and/or the pivot axis of the actuating element 39 preferably extends at right angles or perpendicularly thereto.

According to a particularly preferred alternative embodiment, however, the pivot axis of the actuating element 39 preferably extends substantially parallel thereto.

Particularly preferably, the actuating element 39 is arranged on the side of the inhaler 1 or receptacle 41 or grip member 42 which is remote from the trigger element 8. The advantage of this is that, when the inhaler 1 or tensioning device 38 is used, the actuating element 39 can be pulled towards the grip member 42 and towards an operator, who, as already explained, is preferably standing at right angles to the main dispensing direction or longitudinal direction of the add-on device 23 or chamber 24, most preferably on the right-hand side of the inhaler 1. The direction of actuation of the tensioning device 38 or of the actuating element 39 preferably runs counter to the direction of actuation of the trigger element 8 and/or at right-angles or perpendicularly to the main dispensing direction or longitudinal direction of the add-on device 23 or chamber 24.

It is noted that, when operated, the actuating element 39 can also perform a different movement, i.e., some other movement, i.e., an additional movement or linear movement. Depending on the embodiment, the coupling element 43 may also be omitted and the actuating element 39 may for example, act directly on the part 17 or 18 or on some other gear part of the inhaler 1.

FIG. 5 schematically shows a slot 44 for the means for covering or cleaning. In particular, the means may be constructed as a slide which is guided for example, by the add-on device 23, allows the connector 25 or connecting member 25 to be covered, and/or is operable from outside.

It is noted that the grip 42 is preferably formed so as to be pistol-shaped. This applies for all embodiments.

Further, it is also noted that the inhaler 1 can be operated multiple times with one operation after the other, in particular without changing container 3 or refilling the inhaler 1. Preferably, the inhaler 1 contains multiple doses of the medicament 2. This applies for all embodiments.

The proposed inhaler 1 is designed, in particular, for the brief nebulization of the medicament preparation 2, for example, for only one or two breaths. However, it may also be designed or usable for longer or continuous nebulization.

The proposed inhaler 1 makes it possible, in particular, for a plurality of doses to be nebulized and dispensed one after another. This may be done by one-handed operation, in particular. Thus, an operator has the other hand free for holding a person requiring assistance, such as a small child or older person, or an animal such as a horse or the like. This allows particularly universal application.

Some preferred compounds, ingredients and/or formulations of the medicament preparation 2 are listed below.

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

W denotes a betamimetic, combined with an anticholinergic, corticosteroid, PDE4-inhibitor, EGFR-inhibitor or LTD4-antagonist, W denotes an anticholinergic, combined with a betamimetic, corticosteroid, PDE4-inhibitor, EGFR-inhibitor or LTD4-antagonist, W denotes a corticosteroid, combined with a PDE4-inhibitor, EGFR-inhibitor or LTD4-antagonist W denotes a PDE4-inhibitor, combined with an EGFR-inhibitor or LTD4-antagonist W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5,6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol 5-hydroxy-8-(1-hydroxy-2-isopropylaminobutyl)-2H-1,4-benzoxazin-3-(4H)-one 1-(4-amino-3-chloro-5-trifluoromethylphenyl)-2-tert.-butylamino)ethanol 6-hydroxy-8-{1-hydroxy-2-[2-(4-methoxy-phenyl)-1,1-dimethyl-ethylamino]-ethyl}-4H-benzo[1,4]oxazin-3-one 6-hydroxy-8-{1-hydroxy-2-[2-(ethyl 4-phenoxy-acetate)-1,1-dimethyl-ethylamino]-ethyl}-4H-benzo[1,4]oxazin-3-one 6-hydroxy-8-{1-hydroxy-2-[2-(4-phenoxy-acetic acid)-1,1-dimethyl-ethylamino]-ethyl}-4H-benzo[1,4]oxazin-3-one 8-{2-[1,1-dimethyl-2-(2,4,6-trimethylphenyl)-ethylamino]-1-hydroxy-ethyl}-6-hydroxy-4H-benzo[1,4]oxazin-3-one 6-hydroxy-8-{1-hydroxy-2-[2-(4-hydroxy-phenyl)-1,1-dimethyl-ethylamino]-ethyl}-4H-benzo[1,4]oxazin-3-one 6-hydroxy-8-{1-hydroxy-2-[2-(4-isopropyl-phenyl)-1,1dimethyl-ethylamino]-ethyl}-4H-benzo[1,4]oxazin-3-one 8-{2-[2-(4-ethyl-phenyl)-1,1-dimethyl-ethylamino]-1-hydroxy-ethyl}-6-hydroxy-4H-benzo[1,4]oxazin-3-one 8-{2-[2-(4-ethoxy-phenyl)-1,1-dimethyl-ethylamino]-1-hydroxy-ethyl}-6-hydroxy-4H-benzo[1,4]oxazin-3-one 4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid 8-{2-[2-(3,4-difluoro-phenyl)-1,1-dimethyl-ethylamino]-1-hydroxy-ethyl}-6-hydroxy-4H-benzo[1,4]oxazin-3-one 1-(4-ethoxy-carbonylamino-3-cyano-5-fluorophenyl)-2-(tert-butylamino)ethanol 2-hydroxy-5-(1-hydroxy-2-{2-[4-(2-hydroxy-2-phenyl-ethylamino)-phenyl]-ethylamino}-ethyl)-benzaldehyde N-[2-hydroxy-5-(1-hydroxy-2-{2-[4-(2-hydroxy-2-phenyl-ethylamino)-phenyl]-ethylamino}-ethyl)-phenyl]-formamide 8-hydroxy-5-(1-hydroxy-2-{2-[4-(6-methoxy-biphenyl-3-ylamino)-phenyl]-ethylamino}-ethyl)-1H-quinolin-2-one 8-hydroxy-5-[1-hydroxy-2-(6-phenethylamino-hexylamino)-ethyl]-1H-quinolin-2-one 5-[2-(2-{4-[4-(2-amino-2-methyl-propoxy)-phenylamino]-phenyl}-ethylamino)-1-hydroxy-ethyl]-8-hydroxy-1H-quinolin-2-one

[3-(4-{6-[2-hydroxy-2-(4-hydroxy-3-hydroxymethyl-phenyl)-ethylamino]-hexyloxy}-butyl)-5-methyl-phenyl]-urea 4-(2-{6-[2-(2,6-dichloro-benzyloxy)-ethoxy]-hexylamino}-1-hydroxy-ethyl)-2-hydroxymethyl-phenol 3-(4-{6-[2-hydroxy-2-(4-hydroxy-3-hydroxymethyl-phenyl)-ethylamino]-hexyloxy}-butyl)-benzylsulphonamide 3-(3-{7-[2-hydroxy-2-(4-hydroxy-3-hydroxymethyl-phenyl)-ethylamino]-heptyloxy}-propyl)-benzylsulphonamide 4-(2-{6-[4-(3-cyclopentanesulphonyl-phenyl)-butoxy]-hexylamino}-1-hydroxy-ethyl)-2-hydroxymethyl-phenol N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

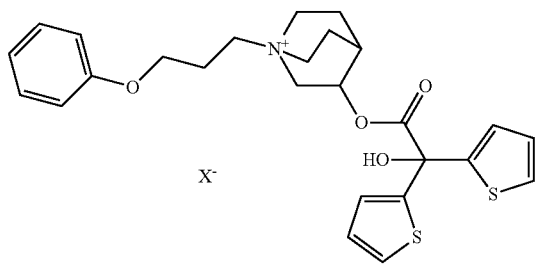

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

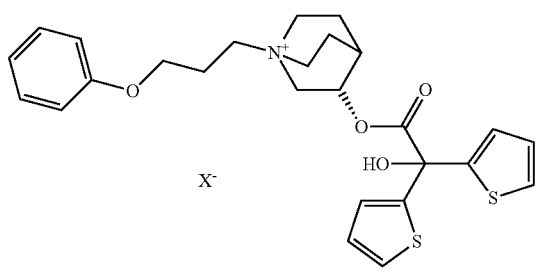

AC-1-en wherein $X^-$ may have the above-mentioned meanings. Other preferred anticholinergics are selected from the salts of formula AC-2

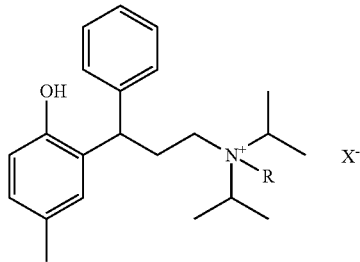

AC-2 wherein R denotes either methyl or ethyl and wherein $X^-$ may have the above-mentioned meanings. In an alternative embodiment the compound of formula AC-2 may also be present in the form of the free base AC-2-base.

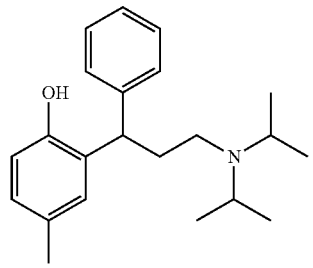

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate methobromide;
scopine 9-methyl-xanthene-9-carboxylate methobromide;
tropenol 9-ethyl-xanthene-9-carboxylate methobromide;

tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the metho-X salts are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and (S)-fluoromethyl 6,9-difluoro-17-[(2-furanylcarbonyl)oxy]-11-hydroxy-16-methyl-3-oxo-androsta-1,4-diene-17-carbothionate (S)-(2-oxo-tetrahydro-furan-3S-yl)6,9-difluoro-11-hydroxy-16-methyl-3-oxo-17-propionyloxy-androsta-1,4-diene-17-carbothionate, cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as for example, sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and N-(3,5-dichloro-1-oxo-pyridin-4-yl)-4-difluoromethoxy-3-cyclopropylmethoxybenzamide (−)p-[(4αR*,10bS*)-9-ethoxy-1,2,3,4,4a,10b-hexahydro-8-methoxy-2-methylbenzo[s][1,6]naphthyridin-6-yl]-N,N-diisopropylbenzamide (R)-(+)-1-(4-bromobenzyl)-4-[(3-cyclopentyloxy)-4-methoxyphenyl]-2-pyrrolidone 3-(cyclopentyloxy-4-methoxyphenyl)-1-(4-N'-[N-2-cyano-S-methyl-isothioureido]benzyl)-2-pyrrolidone cis[4-cyano-4-(3-cyclopentyloxy-4-methoxyphenyl)cyclohexane-1-carboxylic acid]

2-carbomethoxy-4-cyano-4-(3-cyclopropylmethoxy-4-difluoromethoxy-phenyl)cyclohexan-1-one cis[4-cyano-4-(3-cyclopropylmethoxy-4-difluoromethoxyphenyl)cyclohexan-1-ol]

(R)-(+)-ethyl[4-(3-cyclopentyloxy-4-methoxyphenyl)pyrrolidin-2-ylidene]acetate (S)-(−)-ethyl[4-(3-cyclopentyloxy-4-methoxyphenyl)pyrrolidin-2-ylidene]acetate 9-cyclopentyl-5,6-dihydro-7-ethyl-3-(2-thienyl)-9H-pyrazolo[3,4-c]-1,2,4-triazolo[4,3-a]pyridine 9-cyclopentyl-5,6-dihydro-7-ethyl-3-(tert-butyl)-9H-pyrazolo[3,4-c]-1,2,4-triazolo[4,3-a]pyridine optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl] phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example, sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxy-ethyl)-amino)-1-oxo-2-buten-1-yl]amino}-7-cyclopropylmethoxy-quinazoline 4-[(R)-(1-phenyl-ethyl)amino]-6-({4-[N-(2-methoxy-ethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxy-ethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxy-ethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6,7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl)quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxy-carbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline 4-[(3-chloro-4-fluoro-phenyl)amino]-6-(trans-4-methanesulphonylamino-cyclohexan-1-yloxy)-7-methoxy-quinazoline 4-[(3-chloro-4-fluoro-phenyl)amino]-6-(tetrahydropyran-3-yloxy)-7-methoxy-quinazoline 4-[(3-chloro-4-fluoro-phenyl)amino]-6-(1-methyl-piperidin-4-yloxy)-7-methoxy-quinazoline 4-[(3-chloro-4-fluoro-phenyl)amino]-6-{1-[(morpholin-4-yl)carbonyl]-piperidin-4-yl-oxy}-7-methoxy-quinazoline 4-[(3-chloro-4-fluoro-phenyl)amino]-6-{1-[(methoxymethyl)carbonyl]-piperidin-4-yl-oxy}-7-methoxy-quinazoline 4-[(3-chloro-4-fluoro-phenyl)amino]-6-(piperidin-3-yloxy)-7-methoxy-quinazoline 4-[(3-chloro-4-fluoro-phenyl)amino]-6-[1-(2-acetylamino-ethyl)-piperidin-4-yloxy]-7-methoxy-quinazoline 4-[(3-chloro-4-fluoro-phenyl)amino]-6-(tetrahydropyran-4-yloxy)-7-ethoxy-quinazoline 4-[(3-chloro-4-fluoro-phenyl)amino]-6-((S)-tetrahydrofuran-3-yloxy)-7-hydroxy-quinazoline 4-[(3-chloro-4-fluoro-phenyl)amino]-6-(tetrahydropyran-4-yloxy)-7-(2-methoxy-ethoxy)-quinazoline 4-[(3-chloro-4-fluoro-phenyl)amino]-6-{trans-4-[(dimethylamino)sulphonylamino]-cyclohexan-1-yloxy}-7-methoxy-quinazoline 4-[(3-chloro-4-fluoro-phenyl)amino]-6-{trans-4-[(morpholin-4-yl)carbonylamino]-cyclohexan-1-yloxy}-7-methoxy-quinazoline 4-[(3-chloro-4-fluoro-phenyl)amino]-6-{trans-4-[(morpholin-4-yl)sulphonylamino]-cyclohexan-1-yloxy}-7-methoxy-quinazoline 4-[(3-chloro-4-fluoro-phenyl)amino]-6-(tetrahydropyran-4-yloxy)-7-(2-acetylamino-ethoxy)-quinazoline 4-[(3-chloro-4-fluoro-phenyl)amino]-6-(tetrahydropyran-4-yloxy)-7-(2-methanesulphonylamino-ethoxy)-quinazoline 4-[(3-chloro-4-fluoro-phenyl)amino]-6-{1-[(piperidin-1-yl)carbonyl]-piperidin-4-yloxy}-7-methoxy-quinazoline 4-[(3-chloro-4-fluoro-phenyl)amino]-6-(1-aminocarbonylmethyl-piperidin-4-yloxy)-7-methoxy-quinazoline 4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline 4-[(3-chloro-4-fluoro-phenyl)amino]-6-(trans-4-ethanesulphonylamino-cyclohexan-1-yloxy)-7-methoxy-quinazoline 4-[(3-chloro-4-fluoro-phenyl)amino]-6-(1-methanesulphonyl-piperidin-4-yloxy)-7-ethoxy-quinazoline 4-[(3-chloro-4-fluoro-phenyl)amino]-6-(1-methanesulphonyl-piperidin-4-yloxy)-7-(2-methoxy-ethoxy)-quinazoline 4-[(3-chloro-4-fluoro-phenyl)amino]-6-[1-(2-methoxy-acetyl)-piperidin-4-yloxy]-7-(2-methoxy-ethoxy)-quinazoline 4-[(3-chloro-4-fluoro-phenyl)amino]-6-(cis-4-acetylamino-cyclohexan-1-yloxy)-7-methoxy-quinazoline 4-[(3-ethynyl-phenyl)amino]-6-[1-(tert.-butyloxycarbonyl)-piperidin-4-yloxy]-7-methoxy-quinazoline 4-[(3-ethynyl-phenyl)amino]-6-(tetrahydropyran-4-yloxy)-7-methoxy-quinazoline 4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline 4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline 4-[(3-chloro-4-fluoro-phenyl)amino]-6-{cis-4-[(morpholin-4-yl)carbonylamino]-cyclohexan-1-yloxy}-7-methoxy-quinazoline 4-[(3-chloro-4-fluoro-phenyl)amino]-6-{1-[2-(2-oxopyrrolidin-1-yl)ethyl]-piperidin-4-yloxy}-7-methoxy-quinazoline 4-[(3-chloro-4-fluoro-phenyl)amino]-6-{1-[(morpholin-4-yl)carbonyl]-piperidin-4-yloxy}-7-(2-methoxy-ethoxy)-quinazoline 4-[(3-ethynyl-phenyl)amino]-6-(1-acetyl-piperidin-4-yloxy)-7-methoxy-quinazoline 4-[(3-ethynyl-phenyl)amino]-6-(1-methyl-piperidin-4-yloxy)-7-methoxy-quinazoline 4-[(3-ethynyl-phenyl)amino]-6-(1-methanesulphonyl-piperidin-4-yloxy)-7-methoxy-quinazoline 4-[(3-chloro-4-fluoro-phenyl)amino]-6-(1-methyl-piperidin-4-yloxy)-7(2-methoxy-ethoxy)-quinazoline 4-[(3-chloro-4-fluoro-phenyl)amino]-6-(1-isopropyloxycarbonyl-piperidin-4-yloxy)-7-methoxy-quinazoline 4-[(3-chloro-4-fluoro-phenyl)amino]-6-(cis-4-methylamino-cyclohexan-1-yloxy)-7-methoxy-quinazoline 4-[(3-chloro-4-fluoro-phenyl)amino]-6-{cis-4-[N-(2-methoxy-acetyl)-N-methyl-amino]-cyclohexan-1-yloxy}-7-methoxy-quinazoline 4-[(3-ethynyl-phenyl)amino]-6-(piperidin-4-yloxy)-7-methoxy-quinazoline 4-[(3-ethynyl-phenyl)amino]-6-[1-(2-methoxy-acetyl)-piperidin-4-yloxy]-7-methoxy-quinazoline 4-[(3-ethynyl-phenyl)amino]-6-{1-[(morpholin-4-yl)carbonyl]-piperidin-4-yloxy}-7-methoxy-quinazoline 4-[(3-chloro-4-fluoro-phenyl)amino]-6-{1-[(cis-2,6-dimethyl-morpholin-4-yl)carbonyl]-piperidin-4-yloxy}-7-methoxy-quinazoline 4-[(3-chloro-4-fluoro-phenyl)amino]-6-{1-[(2-methyl-morpholin-4-yl)carbonyl]-piperidin-4-yloxy}-7-methoxy-quinazoline 4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline 4-[(3-chloro-4-fluoro-phenyl)amino]-6-{1-[(N-methyl-N-2-methoxyethyl-amino)carbonyl]-piperidin-4-yloxy}-7-methoxy-quinazoline 4-[(3-chloro-4-fluoro-phenyl)amino]-6-(1-ethyl-piperidin-4-yloxy)-7-methoxy-quinazoline 4-[(3-chloro-4-fluoro-phenyl)amino]-6-{1-[(2-methoxyethyl)carbonyl]-piperidin-4-yloxy}-7-methoxy-quinazoline 4-[(3-chloro-4-fluoro-phenyl)amino]-6-{1-[(3-methoxypropyl-amino)-carbonyl]-piperidin-4-yloxy}-7-methoxy-quinazoline 4-[(3-chloro-4-fluoro-phenyl)amino]-6-[cis-4-(N-methanesulphonyl-N-methyl-amino)-cyclohexan-1-yloxy]-7-methoxy-quinazoline 4-[(3-chloro-4-fluoro-phenyl)amino]-6-[cis-4-(N-acetyl-N-methyl-amino)-cyclohexan-1-yloxy]-7-methoxy-quinazoline 4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline 4-[(3-chloro-4-fluoro-phenyl)amino]-6-(1-methanesulphonyl-piperidin-4-yloxy)-7-methoxy-quinazole 4-[(3-chloro-4-fluoro-phenyl)amino]-6-(1-cyano-piperidin-4-yloxy)-7-methoxy-quinazoline Optionally, in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorophenoxamine, dimenhydrinate, diphenhydramine, promethazine, ebastine, desloratidine and meclozine, optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

In addition, inhalable macromolecules as disclosed in EP 1 003 478 A1 or CA 2297174 A1 may also be used.

In addition, the compound may be selected from among the ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

What is claimed is:

1. Portable soft mist inhaler for propellant-free metered nebulization of a medicament preparation, comprising:
   an inhaler body,
   a mechanical pressure generator for pressurizing a supply of medicament preparation located in the inhaler body, the pressure generator having a drive spring for pressure generation, within the inhaler body,
   an expulsion nozzle for receiving a dose of the medicament preparation and for delivering the received dose of the nebulized medicament preparation as an aerosol, and
   a tensioning device for tensioning the drive spring,
      wherein at least the tensioning device is constructed to be operable with one hand, and
      wherein the tensioning device comprises an externally actuatable actuating element mounted to pivot on the inhaler body, and a tensioning element extending into the inhaler body for acting on the drive spring, pivoting movement of the actuating element producing movement of the tensioning element in a manner acting on the tensioning element for producing linear movement of the drive spring.

2. Inhaler according to claim 1, wherein the tensioning device comprises a manually operable actuating element for tensioning the drive spring.

3. Inhaler according to claim 2, wherein said actuating element is pivotable or moveable in a linear manner.

4. Inhaler according to claim 1, wherein the inhaler is adapted for nebulization of a medicament preparation for a horse or other animal.

5. Inhaler according to claim 1, wherein the pressure generator is in the form of a pump.

6. Inhaler according to claim 1, wherein the tensioning device has a pistol grip shape.

7. Portable soft mist inhaler for propellant-free metered nebulization of a medicament preparation, comprising:
   an inhaler body,
   a container mountable within the inhaler body,
   a mechanical pressure generator for pressurizing a supply of medicament preparation located in said container when the container is mounted within the inhaler body, the pressure generator having a drive spring for pressure generation, the drive spring extending around and being movable relative to said container when the container is mounted within the inhaler body,
   an expulsion nozzle for receiving a dose of the medicament preparation and for delivering the received dose of the nebulized medicament preparation as an aerosol, and
   a tensioning device for tensioning the drive spring,
   wherein at least the tensioning device is constructed to be operable with one hand, and
   wherein the tensioning device comprises an externally actuatable actuating element mounted to pivot on the inhaler body, and a tensioning element extending into the inhaler body for acting on the drive spring, pivoting movement of the actuating element producing movement of the tensioning element in a manner acting on the tensioning element for producing linear movement of the drive spring.

* * * * *